(12) United States Patent
Xu et al.

(10) Patent No.: US 11,338,276 B2
(45) Date of Patent: May 24, 2022

(54) CATALYST FOR PREPARING CHLOROETHYLENE BY CRACKING 1,2-DICHLOROETHANE AND A PREPARATION AND REGENERATION METHOD THEREOF

(71) Applicants: DALIAN INSTITUTE OF CHEMICAL PHYSICS, CHINESE ACADEMY OF SCIENCES, Dalian (CN); FORMOSA PLASTICS CORPORATION, Taiwan (CN)

(72) Inventors: Jinming Xu, Dalian (CN); Sisi Fan, Dalian (CN); Yanqiang Huang, Dalian (CN); Fao Zhang, Dalian (CN); Chin Lien Huang, Kaohsiung (CN); Wan Tun Hung, Kaohsiung (CN); Tu Cheng Chen, Kaohsiung (CN); Chien Hui Wu, Kaohsiung (CN); Ya Wen Cheng, Kaohsiung (CN); Ming Hsien Wen, Kaohsiung (CN); Chao Chin Chang, Kaohsiung (CN); Tsao Cheng Huang, Kaohsiung (CN)

(73) Assignees: DALIAN INSTITUTE OF CHEMICAL PHYSICS, CHINESE ACADEMY OF SCIENCES, Dalian (CN); FORMOSA PLASTICS CORPORATION, Taiwan (CN)

( * ) Notice: Subject to any disclaimer, the term of this patent is extended or adjusted under 35 U.S.C. 154(b) by 0 days.

(21) Appl. No.: 16/643,617

(22) PCT Filed: Apr. 30, 2019

(86) PCT No.: PCT/CN2019/085314
§ 371 (c)(1),
(2) Date: Jun. 8, 2020

(87) PCT Pub. No.: WO2020/220312
PCT Pub. Date: Nov. 5, 2020

(65) Prior Publication Data
US 2020/0346195 A1 Nov. 5, 2020

(51) Int. Cl.
*B01J 27/24* (2006.01)
*C07C 17/25* (2006.01)
(Continued)

(52) U.S. Cl.
CPC ............. *B01J 27/24* (2013.01); *B01J 21/06* (2013.01); *B01J 27/28* (2013.01); *B01J 38/02* (2013.01);
(Continued)

(58) Field of Classification Search
CPC ... B01J 27/24; B01J 21/06; B01J 27/28; B01J 38/02; B01J 38/12; B01J 21/04;
(Continued)

(56) References Cited

U.S. PATENT DOCUMENTS 2,803,680 A * 8/1957 Conrad ................... C07C 21/06
570/227
2,809,221 A * 10/1957 Thomas ................. C07C 17/02
570/235
(Continued)

FOREIGN PATENT DOCUMENTS

CN 104289247 A 1/2015
CN 105749948 A 7/2016
(Continued)

OTHER PUBLICATIONS

Zhao, W. et al. "Catalytic dehydrochlorination of 1,2-dichloroethane to produce vinyl chloride over N-doped coconut activated carbon" RSC Adv., 2015, 5, 104071-104078 (Year: 2015).*
(Continued)

*Primary Examiner* — Patricia L. Hailey
(74) *Attorney, Agent, or Firm* — Maier & Maier, PLLC

(57) ABSTRACT

A catalyst for preparing chloroethylene by cracking 1,2-dichloroethane and a preparation and regeneration method
(Continued)

thereof are disclosed in the present application. A catalyst for preparing chloroethylene by cracking 1,2-dichloroethane includes a carrier and a nitrogen-containing carbon as an active component of the catalyst with the nitrogen-containing carbon being loaded on the carrier. The method for preparing the catalyst includes: supporting an organic matter on an inorganic porous carrier and then performing a carbonization-nitridation process by pyrolysis in an atmosphere containing the nitrogen-containing compound. The method for regenerating the catalyst includes: calcinating the catalyst with deactivated carbon deposit in an oxidizing atmosphere to remove all the carbonaceous portions on the surface, and repeating the above preparation process of the catalyst. The catalyst reduces reaction temperature, reduces energy consumption, reduces production cost, and improves selectivity and conversion rate and is inexpensive and reproducible, and has a long service life.

14 Claims, 1 Drawing Sheet

(51) Int. Cl.
| | |
|---|---|
| *B01J 38/02* | (2006.01) |
| *B01J 27/28* | (2006.01) |
| *B01J 38/12* | (2006.01) |
| *B01J 21/06* | (2006.01) |
| *B01J 21/04* | (2006.01) |
| *B01J 21/08* | (2006.01) |
| *C07C 21/06* | (2006.01) |

(52) U.S. Cl.
CPC .............. *B01J 38/12* (2013.01); *C07C 17/25* (2013.01); *B01J 21/04* (2013.01); *B01J 21/063* (2013.01); *B01J 21/066* (2013.01); *B01J 21/08* (2013.01); *C07C 21/06* (2013.01)

(58) Field of Classification Search
CPC ........ B01J 21/063; B01J 21/066; B01J 21/08; B01J 37/0203; B01J 37/082; B01J 38/485; C07C 17/25; C07C 21/06
USPC ............................................ 502/38, 54, 200
See application file for complete search history.

(56) References Cited

U.S. PATENT DOCUMENTS

| | | | | |
|---|---|---|---|---|
| 3,243,383 A | * | 3/1966 | Schultz ................... | B01J 23/94 502/26 |
| 3,551,506 A | * | 12/1970 | Weinstein ............. | C07C 17/154 570/224 |
| 6,441,257 B1 | * | 8/2002 | Seidelbach ............. | C07C 17/25 570/226 |
| 8,318,125 B2 | * | 11/2012 | Uchida .................... | B01J 38/12 423/502 |
| 2007/0161830 A1 | * | 7/2007 | Strebelle ................. | B01J 23/96 570/245 |
| 2018/0118643 A1 | * | 5/2018 | Garthey ................... | B01J 21/18 |
| 2018/0185833 A1 | * | 7/2018 | Kramer .................. | B01J 23/862 |
| 2021/0252489 A1 | * | 8/2021 | Xu ......................... | B01J 37/349 |

FOREIGN PATENT DOCUMENTS

| | | |
|---|---|---|
| CN | 105833892 A | 8/2016 |
| CN | 105983428 A | 10/2016 |
| CN | 106669757 A | 5/2017 |
| CN | 109 180 421 A | 1/2019 |
| CN | 109926081 A | 6/2019 |
| EP | 0 738 699 A1 | 10/1996 |
| EP | 1 273 336 A2 | 1/2003 |
| EP | 1 273 336 A3 | 5/2003 |
| JP | H09-249590 A | 9/1997 |

OTHER PUBLICATIONS

English translation of the Written Opinion for PCT/CN2019/085314. (Year: 2020).*
International Search Report dated Jan. 17, 2020, in connection with corresponding International Application No. PCT/CN2019/085314 (5 pp., including machine-generated English translation).
Search Report dated Apr. 13, 2021 in corresponding European Application No. 19727276.8; 16 pages.
Zhao et al. "Catalytic dehydrochlorination of 1,2-dichloroethane to produce vinyl chloride over N-doped coconut activated carbon." RSC Advances, Royal Society of Chemistry. vol. 5. 2015. 9 pages.
Xu et al. "Synthesis of nitrogen-doped ordered mesoporous carbons for catalytic dehydrochlorination of 1,2-dichloroethane." ScienceDirect, Carbon. vol. 80. 2014. 8 pages.
Jinming Xu et al. "Synthesis of nitrogen-doped ordered mesoporous carbons for catalytic dehydrochlorination of 1,2-dichloroethane". Carbon, 2014, vol. 80, pp. 610-616; 7 pgs.
Wei Zhao et al. "Catalytic dehydrochlorination of 1,2-dichloroethane to produce vinyl chloride over N-doped coconut activated carbon", RSC Advances, 2015, vol. 5, pp. 104071-104078, 8 pgs.

* cited by examiner

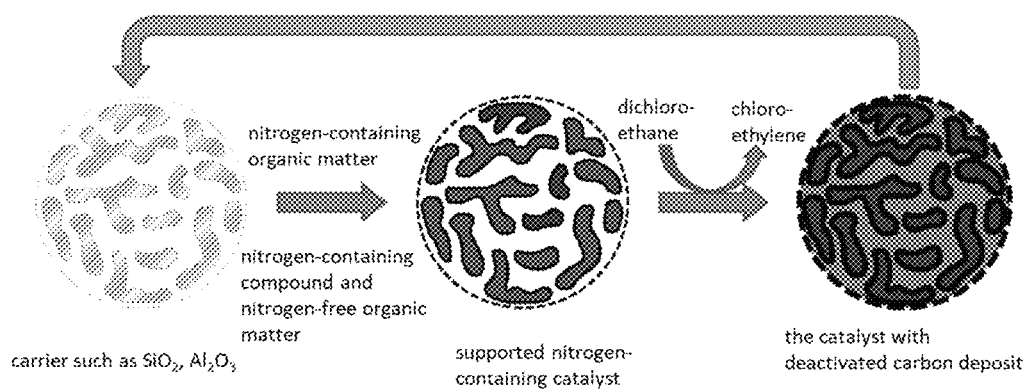

CATALYST FOR PREPARING CHLOROETHYLENE BY CRACKING 1,2-DICHLOROETHANE AND A PREPARATION AND REGENERATION METHOD THEREOF

FIELD

The invention belongs to the field of catalyst, and particularly relates to a catalyst for preparing chloroethylene by cracking 1,2-dichloroethane and a preparation and regeneration method thereof.

BACKGROUND

Chloroethylene is an important polymerized monomer used in polymer chemical industry. At present, the industrial production process of chloroethylene mainly includes ethylene method and acetylene method. Mercuric chloride is generally used as a catalyst to produce polyvinyl chloride in the carbide acetylene method, which will not only generate a large amount of carbide slag and waste water to increase investment cost, but also cause pollution to the environment and poses a hazard to human health. The ethylene method for preparing chloroethylene is now the world recognized energy-saving and environmentally-friendly advanced production route. There are three main processes in the ethylene method. In the first step, light diesel oil or chemical light oil in crude oil is cracked to obtain ethylene. In the second step, a chlorination or oxychlorination reaction of ethylene is carried out directly to generate 1,2-dichloroethane. In the third step, chloroethylene is prepared by cracking 1,2-dichloroethane in a high temperature tubular cracking furnace. Therefore, the cracking of 1,2-dichloroethane is a crucial step in the ethylene method. The industrial reaction temperature is usually in a range from 500° C. to 600° C., and the conversion rate of 1,2-dichloroethane is controlled at about 50% in this case. Due to high temperature thermal cracking reaction is high in reaction temperature, great in energy consumption and easy for coking, the cracking furnace and subsequent separation process equipment are blocked by coking particles, thus a series of problems will occur such as requiring frequent coking and a short production cycle. The nitrogen-containing carbon catalyst can catalyze the cracking of 1,2-dichloroethane, which can reduce the cracking temperature to a lower temperature of being in a range from 250° C. to 350° C. and improve the selectivity to chloroethylene (Jinming Xu et al. "Synthesis of nitrogen-doped ordered mesoporous carbons for catalytic dehydrochlorination of 1,2-dichloroethane". «Carbon». 2014, Vol. 80, pp. 610-616; Wei Zhao et al. "Catalytic dehydrochlorination of 1,2-dichloroethane to produce vinyl chloride over N-doped coconut activated carbon". «RSC Advances». 2015, Vol. 5, pp. 104071-104078).

In the Chinese invention patent with an application No. of 201610256390.8, a catalyst with activated carbon as a carrier for supporting a nitrogen-containing compound is proposed, which can reduce the temperature of current industrial thermal cracking for preparing chloroethylene from a temperature ranges from 50° C. to 500° C. to a temperature ranges from 280° C. to 300° C., the single-pass conversion rate of 1,2-dichloroethane can be increased from 50% to 93%, but the catalyst is short in service life as it will lose activity in only 100 hours.

From the viewpoint of the porous carbon catalysts which have been reported, there are disadvantages such as high in cost, short in life, and difficulty in regeneration, and thus industrial application has not been realized yet.

SUMMARY

In order to solve the problems in the prior art, especially in comparison with the existing thermal cracking technology, the object of the present invention is to provide a catalyst which could reduce the reaction temperature, greatly reduce energy consumption, reduce the production cost, and improve the selectivity and conversion rate and is inexpensive and reproducible, and has a long service life.

The overall concept of the present invention is to provide a catalyst for preparing chloroethylene by cracking 1,2-dichloroethane, the catalyst comprises a carrier and a nitrogen-containing carbon as an active component of the catalyst with the nitrogen-containing carbon being loaded on the carrier. The catalyst is prepared by the following steps: supporting an organic matter on an inorganic porous carrier and then performing a carbonization-nitridation process by pyrolysis in an atmosphere containing the nitrogen-containing compound. The catalyst can be regenerated by the following steps: calcinating the catalyst with deactivated carbon deposit in an oxidizing atmosphere to remove all the carbonaceous portions on the surface to re-use as a carrier, and repeating the preparation process of the catalyst. See FIG. 1 for details.

A catalyst for preparing chloroethylene by cracking 1,2-dichloroethane is provided according to one aspect of the present invention, the catalyst comprises a carrier and a nitrogen-containing carbon material as an active component of the catalyst, the nitrogen-containing carbon material is supported on the carrier; the carrier is at least one selected from inorganic porous materials; a nitrogen element is doped in a carbon material in a form of covalent bond in the nitrogen-containing carbon material.

Those skilled in the art can modulate the content of nitrogen element in the nitrogen-containing carbon material by using the method provided in the present invention according to actual needs.

Optionally, the mass percentage of the nitrogen element in the nitrogen-containing carbon material is in a range from 0.1% to 20%.

Preferably, the mass percentage of the nitrogen element in the nitrogen-containing carbon material is in a range from 1% to 9%.

Those skilled in the art can modulate the content of the nitrogen-containing carbon material in the catalyst by using the method provided in the present invention according to actual needs.

Optionally, the mass percentage of the nitrogen-containing carbon material in the catalyst is in a range from 1% to 40%.

Preferably, the mass percentage of the nitrogen-containing carbon material in the catalyst is in a range from 8% to 30%.

Optionally, the inorganic porous material is at least one selected from the group consisting of silicon oxide, aluminum oxide, titanium oxide, and zirconium oxide.

According to still another aspect of the present invention, a preparation method of the catalyst for preparing chloroethylene by cracking 1,2-dichloroethane mentioned above is provided, wherein the method comprises at least the following steps: firstly, supporting an organic precursor on an inorganic porous material and then a carrying out a carbonization-nitridation reaction by pyrolysis in an atmosphere containing the nitrogen-containing compound.

Optionally, the pyrolysis conditions are: a pyrolysis temperature in a range from 400° C. to 1000° C., and a pyrolysis time in a range from 0.2 hour to 10 hours.

Preferably, the pyrolysis conditions are: a pyrolysis temperature in a range from 600° C. to 900° C., and a pyrolysis time in a range from 0.5 hour to 6 hours.

The atmosphere containing the nitrogen-containing compound may be a pure nitrogen-containing compound gas or may contain an inactive gas. The inactive gas is at least one selected from the group consisting of nitrogen, argon gas and helium gas.

As an embodiment, when the atmosphere containing the nitrogen-containing compound contains an inactive gas, the mass content of the nitrogen-containing compound in the mixed gas is in a range from 0.5% to less than 100%.

In principle, a compound containing a nitrogen element which can be vaporized can be used as the nitrogen-containing compound in the present invention.

Optionally, the nitrogen-containing compound is at least one selected from the group consisting of ammonia gas, hydrazine, an organic compound containing a C—N bond, an organic compound containing C=N, and an organic compound containing C≡N.

Preferably, the nitrogen-containing compound is at least one selected from the group consisting of ammonia gas, hydrazine, acetonitrile, cyanamide, pyridine, pyrrole, ethylenediamine or methylamine.

In principle, the organic compound which can be vaporized or vaporized after dissolution can be used as the organic precursor in the present invention and used as a carbon source in the preparation of the catalyst.

Optionally, the organic precursor is at least one selected from the group consisting of hydrocarbon compound, polymer, an organic compound containing at least one group of *—CX, *—OH, *—C≡N, *—C=O, *—C—O—* bond, *—C—NH$_2$, *—C—NH—C—*, *—C—N=C—*.

Wherein X in *—CX represents a halogen, which is at least one selected from the group consisting of F, Cl, Br, and I.

Optionally, the organic precursor is at least one selected from the group consisting of a hydrocarbon with 1 to 18 carbon atoms, a halogenated hydrocarbon, an alcohol, an ether, an ester, a ketone, an amine, an acid, a phenol, a nitrile, a furan, a pyridine and a pyrrole.

The organic matter may specifically be at least one selected from the group consisting of acrylonitrile, chloroethylene, dichloroethylene, vinylpyridine, acrylamide, acrylic compounds, vinyl ester compounds, aniline compounds, pyrrolic compounds, urea resin, phenol resin, melamine resin, polyurethane and furan resin in a form of a monomer or polymer, glucose, fructose, xylose, sucrose, dextran, lignin, organic pyrolysis oil and pitch.

Wherein, when the organic precursor is a polymer, the polymer has a weight average molecular weight of less than 20,000 and is soluble in water or a liquid organic solvent.

Optionally, the method for supporting the organic precursor on the inorganic porous material is at least one selected from the following methods:
(i) impregnation method;
(ii) spraying method.

According to still another aspect of the present application, provided is a method for regenerating the catalyst for preparing chloroethylene by cracking 1,2-dichloroethane mentioned above, wherein the regeneration method comprises: calcinating a deactivated catalyst in an atmosphere containing oxygen after the catalyst is deactivated in a catalytic cracking reaction of 1,2-dichloroethane for preparing chloroethylene; using the solid obtained after calcination as a carrier to prepare a regenerated catalyst according to the above preparation method of the catalyst for preparing chloroethylene by cracking 1,2-dichloroethane.

Optionally, the calcination conditions are: a calcination temperature in a range from 300° C. to 800° C., and a calcination time in a range from 0.2 hour to 10 hours.

Preferably, the calcination conditions are: a calcination temperature in a range from 450° C. to 700° C., and a calcination time in a range from 0.5 hour to 6 hours.

According to still another aspect of the present application, a method for preparing chloroethylene by cracking 1,2-dichloroethane is provided, comprising passing a feed gas containing 1,2-dichloroethane through a fixed bed reactor supported with a catalyst to prepare chloroethylene.

The catalyst is at least one selected from any one of catalysts mentioned above for preparing chloroethylene by cracking 1,2-dichloroethane.

Advantages of the invention include, but are not limited to:

(1) the catalyst provided by the present invention is used in a cracking reaction of 1,2-dichloroethane to prepare chloroethylene, which greatly reduces the reaction temperature and energy consumption compared with the conventional thermal cracking method, thereby reducing the production cost.

(2) the catalyst provided by the invention with a less content of nitrogen-containing carbon as an active component of catalyst and the inorganic porous material acts as a carrier of the catalyst has a high catalyst strength while ensuring catalyst activity.

3) the preparation method of the catalyst provided by the present invention is simple and easy to operate and is advantageous for large-scale industrial production;

(4) the reuse of the inorganic porous material could be achieved in the method for regenerating a catalyst provided by the present invention by calcining the deactivated catalyst, removing the carbonaceous portion on the surface of the carrier, reloading the active component to restore the activity of the catalyst, thereby the reuse of the inorganic porous material could be achieved and the preparation cost of the catalyst could be greatly reduced. Thus, the catalyst has great industrial application prospects.

BRIEF DESCRIPTION OF THE DRAWINGS

FIG. 1 is a schematic illustration of the catalyst of the present invention, the preparation, application and regeneration process thereof.

DETAILED DESCRIPTION

The technical solutions of the present application will be further described below with reference to the examples. The following examples are only some of the preferred embodiments of the present invention, and the present invention is not limited to the contents of the embodiments. It will be apparent to those skilled in the art that various changes and modifications may be made within the scope of the concept of the technical solution of the present invention. Any changes and modifications made are within the scope of the present invention.

In the examples, the silica gel pellet is purchased from Qingdao Ocean Chemical Co., Ltd., and the silica gel pellet has a particle diameter in a range from 2 mm to 4 mm a colour of white.

In the examples, the conversion rate of 1,2-dichloroethane is calculated according to the following method: the conversion rate of 1,2-dichloroethane=the molar number of 1,2-dichloroethane (mol) consumed in the reaction/the molar number of 1,2-dichloroethane (mol) introduced into the reactor.

The selectivity to vinyl chloride is calculated according to the following method:

Selectivity of chloroethylene=the molar number of chloroethylene (mol) generated in the reaction/the molar number of 1,2-dichloroethane (mol) consumed in the reaction.

x-ray photoelectron spectroscopy is measured using an ESCALAB 250Xi instrument.

EXAMPLE 1

Preparation of Nitrogen-Containing Carbon Catalyst Sample CAT-1[#]

0.4 g of oxalic acid was added into 40 mL of furan methanol at room temperature, dissolved, and then 60 mL of xylene was added. 150 mL of silica gel pellet was added into the beaker and immersed for 6 hours, filtered, and heated to 90° C. to carry out a polymerization reaction for 12 hours. Precursor I was obtained.

The precursor I was placed in a quartz tube, then the quartz tube was placed in a tube furnace, nitrogen gas was introduced into the quartz tube, and heated to a temperature of 450° C., and the temperature was maintained for 3 hours. The gas path was switched for introducing ammonia gas into the quartz tube, and then the temperature was raised to 600° C. at a heating rate of 5° C./min and maintained for 3 hours to perform a carbonization-nitridation process to obtain the catalyst, which was designated as sample CAT-1[#]. The mass percentage of the nitrogen element in the supported nitrogen-containing carbon material was 6.5%.

Activity Test of Supported Nitrogen-Containing Carbon Catalyst Sample CAT-1[#]

1,2-dichloroethane liquid was preheated and vaporized in the evaporator, and then introduced into a fixed bed reactor loaded with the catalyst CAT-1[#] by a constant flow pump, the temperature of reactor was 260° C., the volumetric space velocity (GHSV) of 1,2-dichloroethane was 180 h$^{-1}$. The test results showed that the conversion rate of dichloroethane was 54% and the selectivity to chloroethylene was more than 99%.

Regeneration and Activity Test of Catalyst Sample CAT-1[#]

The deactivated catalyst was calcined in air for 1 hour at 600° C., and the obtained solid sample was designated as sample ZCAT-1[#]-Z1.

The silica gel pellet was replaced by the sample ZCAT-1[#]-Z1, and the other preparation steps and conditions were the same as the sample CAT-1[#], and the obtained regenerated catalyst was designated as the sample ZCAT-1[#]-1.

1,2-dichloroethane liquid was preheated and vaporized in the evaporator, and then introduced into a fixed bed reactor supported with the catalyst ZCAT-1[#]-1 by a constant flow pump, the temperature of reactor was 260° C., the volumetric space velocity (GHSV) of 1,2-dichloroethane was 180 h$^{-1}$. The test results showed that the catalytic activity of ZCAT-1[#]-1 was not lowered as compared with CAT-1[#].

EXAMPLE 2

Preparation of Nitrogen-Containing Carbon Catalyst Sample CAT-2[#]

The preparation method of this example was the same as that of Example 1 except that the treatment conditions of ammonia gas in the carbonization-nitridation process were at a temperature of 800° C. and maintained for 1.5 hours. The obtained catalyst was designated as sample CAT-2[#]. The mass percentage of the nitrogen element in the supported nitrogen-containing carbon material was 9%.

Activity Test of Supported Nitrogen-Containing Carbon Catalyst Sample CAT-2[#]

The activity test process differed from Example 1 only in that the temperature of reactor was 260° C. and the volumetric space velocity (GHSV) of 1,2-dichloroethane was 157 h$^{-1}$. The test results showed that the conversion rate of dichloroethane was 72% and the selectivity to chloroethylene was more than 99%.

Regeneration and Activity Test of Catalyst Sample CAT-2[#]

The deactivated catalyst was calcined in air for 1 hour at 450° C., and the obtained solid sample was designated as sample ZCAT-2[#]-Z1.

The silica gel pellet was replaced by the sample ZCAT-2[#]-Z1, and the other preparation steps and conditions were the same as the sample CAT-2[#], and the obtained regenerated catalyst was designated as the sample ZCAT-2[#]-1.

1,2-dichloroethane liquid was preheated and vaporized in the evaporator, and then introduced into a fixed bed reactor supported with the catalyst ZCAT-2[#]-1 by a constant flow pump, the temperature of reactor was 260° C., the volumetric space velocity (GHSV) of 1,2-dichloroethane was 157 h$^{-1}$.

The test results showed that the catalytic activity of ZCAT-2[#]-1 was not lowered as compared with CAT-2[#].

EXAMPLE 3

Preparation of Nitrogen-Containing Carbon Catalyst Sample CAT-3[#]

The preparation method of this example was the same as that of Example 1 except that the amount of furan methanol was 25 mL, the amount of oxalic acid was 0.25 g, and the amount of xylene was 75 mL. The obtained catalyst was designated as sample CAT-3 #. The mass percentage of the nitrogen element in the supported nitrogen-containing carbon material was 7%.

Activity Test of Supported Nitrogen-Containing Carbon Catalyst Sample CAT-3[#]

The activity test process differed from Example 1 only in that the temperature of reactor was 240° C. and the volumetric space velocity (GHSV) of 1,2-dichloroethane was 171 h$^{-1}$. The test results showed that the conversion rate of dichloroethane was 36% and the selectivity to chloroethylene was more than 99% under the action of nitrogen-containing carbon catalyst 3[#].

Regeneration and Activity Test of Catalyst Sample CAT-3[#]

The deactivated catalyst was calcined in air for 0.25 hour at 700° C., and the obtained solid sample was designated as sample ZCAT-3[#]-Z1.

The silica gel pellet was replaced by the sample ZCAT-3[#]-Z1, and the other preparation steps and conditions were the same as the sample CAT-3[#], and the obtained regenerated catalyst was designated as the sample ZCAT-3[#]-1.

1,2-dichloroethane liquid was preheated and vaporized in the evaporator, and then introduced into a fixed bed reactor supported with the catalyst ZCAT-3[#]-1 by a constant flow pump, the temperature of reactor was 240° C., the volumetric space velocity (GHSV) of 1,2-dichloroethane was 171 $h^{-1}$.

The test results showed that the catalytic activity of ZCAT-3#-1 was not lowered as compared with CAT-3#.

EXAMPLE 4

Preparation of Nitrogen-Containing Carbon Catalyst Sample CAT-4 #

50 g of alumina was placed in a 100 g of aqueous solution containing 25 g of sucrose, and the water was evaporated to dryness at 100° C. to obtain a precursor 4.

The precursor 4 was placed in a quartz tube and then the quartz tube was placed in a tube furnace. Argon gas containing 1% (mass percentage) of pyridine was introduced into the quartz tube and heated to 800° C. and the temperature was maintained for 3 hours to perform a carbonization-nitridation process to obtain the catalyst, which was designated as sample CAT-4#. The mass percentage of the nitrogen element in the supported nitrogen-containing carbon material was 4%.

Activity Test of Supported Nitrogen-Containing Carbon Catalyst Sample CAT-4 #

The activity test process differed from Example 1 only in that the temperature of reactor was 260° C. and the volumetric space velocity (GHSV) of 1,2-dichloroethane was 133 $h^{-1}$. The test results showed that the conversion rate of dichloroethane was 54% and the selectivity to chloroethylene was more than 99%.

Regeneration and Activity Test of Catalyst Sample CAT-4#

The deactivated catalyst was calcined in a mixed atmosphere containing 15% $O_2$ and 85% $N_2$ for 2 hours at 600° C., and the obtained solid sample was designated as sample ZCAT-4#-Z1.

The silica gel pellet was replaced by the sample ZCAT-4#-Z1, and the other preparation steps and conditions were the same as the sample CAT-4#, and the obtained regenerated catalyst was designated as the sample ZCAT-4#-1.

1,2-dichloroethane liquid was preheated and vaporized in the evaporator, and then introduced into a fixed bed reactor supported with the catalyst ZCAT-4#-1 by a constant flow pump, the temperature of reactor was 260° C., the volumetric space velocity (GHSV) of 1,2-dichloroethane was 133 $h^{-1}$.

The test results showed that the catalytic activity of ZCAT-4#-1 was not lowered as compared with CAT-4#.

EXAMPLE 5

Preparation of Nitrogen-Containing Carbon Catalyst Sample CAT-5#

50 g of zirconium oxide was placed in 100 g of anhydrous ethanol solution containing 15 g of phenolic resin, and anhydrous ethanol was evaporated to dryness at 80° C. to obtain a precursor 5.

The precursor 5 was placed in a quartz tube and then the quartz tube was placed in a tube furnace. Nitrogen gas containing 5% (mass percentage) of acetonitrile was introduced into the quartz tube and heated to 750° C. and the temperature was maintained for 3 hours to perform a carbonization-nitridation process. Thereafter, the catalyst was obtained and designated as sample CAT-5#. The mass percentage of the nitrogen element in the supported nitrogen-containing carbon material was 2%.

Activity Test of Supported Nitrogen-Containing Carbon Catalyst Sample CAT-5#

The activity test process differed from Example 1 only in that the temperature of reactor was 250° C. and the volumetric space velocity (GHSV) of 1,2-dichloroethane was 133 $h^{-1}$. The test results showed that the conversion rate of dichloroethane was 36% and the selectivity to chloroethylene was more than 99%.

Regeneration and Activity Test of Catalyst Sample CAT-5#

The deactivated catalyst was calcined in air for 2 hours at 600° C., and the obtained solid sample was designated as sample ZCAT-5#-Z1.

The silica gel pellet was replaced by the sample ZCAT-5#-Z1, and the other preparation steps and conditions were the same as the sample CAT-5#, and the obtained regenerated catalyst was designated as the sample ZCAT-5#-1.

1,2-dichloroethane liquid was preheated and vaporized in the evaporator, and then introduced into a fixed bed reactor supported with the catalyst ZCAT-5#-1 by a constant flow pump, the temperature of reactor was 260° C., the volumetric space velocity (GHSV) of 1,2-dichloroethane was 133 $h^{-1}$.

The test results showed that the catalytic activity of ZCAT-5#-1 was not lowered as compared with CAT-5#.

EXAMPLE 6

XPS Characterization of Catalyst Sample CAT-1#~CAT-5 #

The sample CAT-1#~CAT-5# was analyzed by x-ray photoelectron spectroscopy, and the results are showed as follows:

There are at least five nitrogen-containing functional groups in CAT-1#~CAT-5#: pyridine type functional group (398.6 eV), amine or amide type group (399.6 eV), pyrrole type group (400.3 eV), substituted type N atom (401.3 eV, N replaces a C atom in the graphite sheet framework), pyridine oxide type functional group (398.6 eV), indicating that the nitrogen element is doped in the carbon material in a form of covalent bond.

The above are only a few embodiments of the present application, and are not intended to limit the present application in any form. Although the present application is disclosed by the preferred embodiments as above, they are however not used to limit the present application. A slight change or modification utilizing the technical content disclosed above made by the person skilled in art, without departing from the technical solution of the present application, is equivalent to the equivalent embodiment, and falls within the scope of the technical solution.

What is claimed is:

1. A regeneration method of the catalyst for preparing chloroethylene by cracking 1,2-dichloroethane comprising a carrier and a nitrogen-containing carbon material as an active component of the catalyst; and the nitrogen-containing carbon material is loaded on the carrier; the carrier is at least one selected from inorganic porous materials; in the nitrogen-containing carbon material, a nitrogen element is doped in the carbon material in a form of covalent bond, the regeneration method comprising:

calcinating a deactivated catalyst in an atmosphere containing oxygen after deactivating the catalyst in a catalytic cracking reaction of 1,2-dichloroethane for preparing chloroethylene; using the solid obtained after calcination as a carrier to prepare a regenerated catalyst according to a preparation method in supporting an organic precursor on the inorganic porous material of the solid as the carrier and then carrying out a carbonization-nitridation reaction by pyrolysis in an atmosphere containing a nitrogen-containing compound;

wherein the inorganic porous material is at least one selected from the group consisting of silicon oxide, aluminum oxide, titanium oxide, and zirconium oxide.

2. The regeneration method according to claim 1, wherein the calcination conditions are: a calcination temperature in a range from 300° C. to 800° C., and a calcination time in a range from 0.2 hour to 10 hours.

3. The regeneration method according to claim 1, wherein the calcination conditions are: a calcination temperature in a range from 450° C. to 700° C. and a calcination time in a range from 0.5 hour to 6 hours.

4. The regeneration method according to claim 1, wherein the mass percentage of the nitrogen element in the nitrogen-containing carbon material is in a range from 0.1% to 20%.

5. The regeneration method according to claim 1, wherein the mass percentage of the nitrogen element in the nitrogen-containing carbon material is in a range from 1% to 9%.

6. The regeneration method according to claim 1, wherein the mass percentage of the nitrogen-containing carbon material in the catalyst is in a range from 1% to 40%.

7. The regeneration method according to claim 1, wherein the mass percentage of the nitrogen-containing carbon material in the catalyst is in a range from 8% to 30%.

8. The regeneration method according to claim 1, wherein the pyrolysis conditions are: a pyrolysis temperature in a range from 400° C. to 1000° C., and a pyrolysis time in a range from 0.2 hour to 10 hours.

9. The regeneration method according to claim 1, wherein the pyrolysis conditions are: a pyrolysis temperature in a range from 600° C. to 900° C., and a pyrolysis time in a range from 0.5 hour to 6 hours.

10. The regeneration method according to claim 1, wherein the nitrogen-containing compound is at least one selected from the group consisting of ammonia gas, hydrazine, an organic compound containing a C—N bond, an organic compound containing C=N, and an organic compound containing C≡N.

11. The regeneration method according to claim 1, wherein the nitrogen-containing compound is at least one selected from the group consisting of ammonia gas, hydrazine, acetonitrile, cyanamide, pyridine, pyrrole, ethylenediamine or methylamine.

12. The regeneration method according to claim 1, wherein the organic precursor is at least one selected from the group consisting of hydrocarbon compound, polymer, an organic compound containing at least one group of *—CX, *—OH, *—C≡N, *—C≡N, *—C—O—* bond, *—C—NH$_2$, *—C—NH—C—*, *—C—N—C—*;

wherein X in *—CX represents a halogen, which is at least one selected from the group consisting of F, Cl, Br, and I.

13. The regeneration method according to claim 1, wherein the organic precursor is at least one selected from the group consisting of acrylonitrile, chloroethylene, dichloroethylene, vinylpyridine, acrylamide, acrylic compounds, vinyl ester compounds, aniline compounds, pyrrolic compounds, urea resin, phenol resin, melamine resin, polyurethane and furan resin in a form of a monomer or polymer, glucose, fructose, xylose, sucrose, dextran, lignin, organic pyrolysis oil and pitch.

14. The regeneration method according to claim 1, wherein the method for supporting the organic precursor on the inorganic porous material is at least one selected from the following methods:

(i) an impregnation method;
(ii) a spraying method.

* * * * *